(12) United States Patent
Trull et al.

(10) Patent No.: US 7,624,487 B2
(45) Date of Patent: Dec. 1, 2009

(54) APPARATUS AND METHOD FOR FORMING BARBS ON A SUTURE

(75) Inventors: Michael Trull, Apex, NC (US); Perry Genova, Chapel Hill, NC (US); Robert C. Williams, III, Raleigh, NC (US)

(73) Assignee: Quill Medical, Inc.

( * ) Notice: Subject to any disclaimer, the term of this patent is extended or adjusted under 35 U.S.C. 154(b) by 96 days.

(21) Appl. No.: 10/437,144

(22) Filed: May 13, 2003

(65) Prior Publication Data

US 2004/0226427 A1 Nov. 18, 2004

(51) Int. Cl.
*B21F 25/00* (2006.01)
*B26D 7/14* (2006.01)
*A61B 17/04* (2006.01)

(52) U.S. Cl. .............................. 29/7.1; 83/651; 606/228

(58) Field of Classification Search .................... 29/7.1, 29/7.2, 7.3; 606/228, 215, 224, 216; 83/651
See application file for complete search history.

(56) References Cited

U.S. PATENT DOCUMENTS

| | | | |
|---|---|---|---|
| 709,392 A | 9/1902 | Brown |
| 733,723 A | 7/1903 | Lukens |
| 789,401 A | 5/1905 | Acheson |
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,728,316 A | 9/1929 | Von Wachenfeldt |
| 1,886,721 A | 11/1932 | O'Brien |
| 2,201,610 A | 5/1940 | Dawson, Jr. |
| 2,232,142 A | 2/1941 | Schumann |
| 2,254,620 A | 9/1941 | Miller |
| 2,355,907 A | 8/1944 | Cox |
| 2,421,193 A | 5/1947 | Gardner |
| 2,472,009 A | 5/1949 | Gardner |

(Continued)

FOREIGN PATENT DOCUMENTS

CN 2640420 9/2004

(Continued)

OTHER PUBLICATIONS

McKenzie, A.R., "An Experimental Multiple Barbed Suture for the Long Flexor Tendons of the Palm and Fingers"; *The Journal of Bone and Joint Surgery*, vol. 49B, No. 3, Aug. 1967 pp. 440-447.

(Continued)

*Primary Examiner*—John C Hong
(74) *Attorney, Agent, or Firm*—Angiotech

(57) ABSTRACT

An apparatus for cutting barbs into a suture having a filament supply. The apparatus also has an in-feed collet for holding one end of a filament threaded therethrough. Further the apparatus has an out-feed collet for holding a second end of a filament threaded therethrough. Additionally, the apparatus has a holder positioned between said in-feed and out-feed collets for holding a filament suspended between the in-feed and out-feed collets. The apparatus also has a cutting assembly for cutting barbs in the filament tensioned between the in-feed and out-feed collets.

41 Claims, 13 Drawing Sheets

U.S. PATENT DOCUMENTS

| | | | |
|---|---|---|---|
| 2,572,936 A | 10/1951 | Kulp et al. | |
| 2,684,070 A | 7/1954 | Kelsey | |
| 2,779,083 A | 1/1957 | Eaton | |
| 2,814,296 A | 11/1957 | Samuel | |
| 2,817,339 A | 12/1957 | Sullivan | |
| 2,866,256 A | 12/1958 | Matlin | |
| 2,910,067 A | 10/1959 | White | |
| 2,988,028 A | 6/1961 | Alcamo | |
| 3,003,155 A | 10/1961 | Mielzynski et al. | |
| 3,068,869 A | 12/1962 | Shelden et al. | |
| 3,068,870 A | 12/1962 | Levin | |
| 3,123,077 A * | 3/1964 | Alcamo | 606/228 |
| 3,166,072 A | 1/1965 | Sullivan, Jr. | |
| 3,209,754 A | 10/1965 | Brown | |
| 3,214,810 A | 11/1965 | Mathison | |
| 3,221,746 A | 12/1965 | Noble | |
| 3,234,636 A | 2/1966 | Brown | |
| 3,273,562 A | 9/1966 | Brown | |
| 3,352,191 A | 11/1967 | Crawford | |
| 3,378,010 A | 4/1968 | Codling et al. | |
| 3,385,299 A | 5/1968 | LeRoy | |
| 3,494,006 A | 2/1970 | Brumlik | |
| 3,525,340 A | 8/1970 | Gilbert | |
| 3,527,223 A | 9/1970 | Shein | |
| 3,586,002 A | 6/1971 | Wood | |
| 3,608,095 A | 9/1971 | Barry | |
| 3,608,539 A | 9/1971 | Miller | |
| 3,646,615 A | 3/1972 | Ness | |
| 3,683,926 A | 8/1972 | Suzuki | |
| 3,700,433 A | 10/1972 | Duhl | |
| 3,716,058 A | 2/1973 | Tanner, Jr. | |
| 3,720,055 A | 3/1973 | de Mestral et al. | |
| 3,825,010 A | 7/1974 | McDonald | |
| 3,833,972 A | 9/1974 | Brumlik | |
| 3,845,641 A | 11/1974 | Waller | |
| 3,918,455 A | 11/1975 | Coplan | |
| 3,981,051 A | 9/1976 | Brumlik | |
| 3,981,307 A | 9/1976 | Borysko | |
| 4,006,747 A | 2/1977 | Kronenthal et al. | |
| 4,069,825 A | 1/1978 | Akiyama | |
| 4,073,298 A | 2/1978 | LeRoy | |
| 4,198,734 A | 4/1980 | Brumlik | |
| 4,259,959 A | 4/1981 | Walker | |
| 4,300,424 A * | 11/1981 | Flinn et al. | 83/374 |
| 4,311,002 A * | 1/1982 | Hoffmann et al. | 57/293 |
| 4,316,469 A | 2/1982 | Kapitanov | |
| 4,317,451 A | 3/1982 | Cerwin et al. | |
| 4,428,376 A | 1/1984 | Mericle | |
| 4,430,998 A | 2/1984 | Harvey et al. | |
| 4,434,796 A | 3/1984 | Karapetian et al. | |
| 4,454,875 A | 6/1984 | Pratt et al. | |
| 4,467,805 A | 8/1984 | Fukuda | |
| 4,492,075 A * | 1/1985 | Faure | 57/5 |
| 4,493,323 A | 1/1985 | Albright et al. | |
| 4,505,274 A | 3/1985 | Speelman | |
| 4,510,934 A | 4/1985 | Batra | |
| 4,531,522 A | 7/1985 | Bedi et al. | |
| 4,548,202 A | 10/1985 | Duncan | |
| 4,610,251 A | 9/1986 | Kumar | |
| 4,635,637 A | 1/1987 | Schreiber | |
| 4,637,380 A | 1/1987 | Orejola | |
| 4,653,486 A | 3/1987 | Coker | |
| 4,669,473 A | 6/1987 | Richards et al. | |
| 4,676,245 A | 6/1987 | Fukuda | |
| 4,719,917 A | 1/1988 | Barrows et al. | |
| 4,751,621 A * | 6/1988 | Jenkins | 362/119 |
| 4,776,337 A | 10/1988 | Palmaz | |
| 4,832,025 A | 5/1989 | Coates | |
| 4,841,960 A | 6/1989 | Garner | |
| 4,873,976 A | 10/1989 | Schreiber | |
| 4,887,601 A | 12/1989 | Richards | |
| 4,895,148 A | 1/1990 | Bays et al. | |
| 4,900,605 A | 2/1990 | Thorgersen et al. | |
| 4,905,367 A | 3/1990 | Pinchuk et al. | |
| 4,930,945 A * | 6/1990 | Arai et al. | 407/40 |
| 4,948,444 A | 8/1990 | Schutz et al. | |
| 4,950,285 A | 8/1990 | Wilk | |
| 4,976,715 A | 12/1990 | Bays et al. | |
| 4,981,149 A | 1/1991 | Yoon et al. | |
| 4,994,073 A | 2/1991 | Green | |
| 4,997,439 A | 3/1991 | Chen | |
| 5,002,562 A | 3/1991 | Oberlander | |
| 5,007,921 A | 4/1991 | Brown | |
| 5,007,922 A | 4/1991 | Chen et al. | |
| 5,026,390 A | 6/1991 | Brown | |
| 5,047,047 A | 9/1991 | Yoon | |
| 5,053,047 A | 10/1991 | Yoon | |
| 5,084,063 A | 1/1992 | Korthoff | |
| 5,102,418 A | 4/1992 | Granger et al. | |
| 5,102,421 A | 4/1992 | Anspach, Jr. | |
| 5,112,344 A | 5/1992 | Petros | |
| 5,123,911 A | 6/1992 | Granger et al. | |
| 5,123,913 A | 6/1992 | Wilk et al. | |
| 5,123,919 A | 6/1992 | Sauter et al. | |
| 5,127,413 A | 7/1992 | Ebert | |
| 5,133,738 A | 7/1992 | Korthoff | |
| 5,141,520 A | 8/1992 | Goble et al. | |
| 5,156,788 A | 10/1992 | Chesterfield et al. | |
| 5,192,302 A | 3/1993 | Kensey et al. | |
| 5,207,694 A | 5/1993 | Broome | |
| 5,217,494 A | 6/1993 | Coggins et al. | |
| 5,222,976 A | 6/1993 | Yoon | |
| 5,224,946 A | 7/1993 | Hayhurst et al. | |
| 5,246,441 A | 9/1993 | Ross et al. | |
| 5,258,013 A | 11/1993 | Granger et al. | |
| 5,269,783 A | 12/1993 | Sander | |
| 5,292,326 A | 3/1994 | Green et al. | |
| 5,320,629 A | 6/1994 | Noda et al. | |
| 5,330,503 A | 7/1994 | Yoon | |
| 5,341,922 A | 8/1994 | Cerwin et al. | |
| 5,342,376 A | 8/1994 | Ruff | |
| 5,352,515 A | 10/1994 | Jarrett et al. | |
| 5,372,146 A | 12/1994 | Branch | |
| 5,374,268 A | 12/1994 | Sander | |
| 5,374,278 A | 12/1994 | Chesterfield et al. | |
| 5,395,126 A | 3/1995 | Tresslar | |
| 5,411,523 A | 5/1995 | Goble | |
| 5,414,988 A * | 5/1995 | DiPalma et al. | 57/293 |
| 5,425,746 A | 6/1995 | Proto et al. | |
| 5,425,747 A | 6/1995 | Brotz | |
| 5,450,860 A | 9/1995 | O'Connor | |
| 5,500,000 A | 3/1996 | Feagin et al. | |
| 5,500,991 A | 3/1996 | Demarest et al. | |
| 5,520,691 A | 5/1996 | Branch | |
| 5,533,982 A | 7/1996 | Rizk et al. | |
| 5,536,582 A | 7/1996 | Prasad et al. | |
| 5,546,957 A | 8/1996 | Heske | |
| 5,584,859 A | 12/1996 | Brotz | |
| 5,601,557 A | 2/1997 | Hayhurst et al. | |
| 5,683,417 A | 11/1997 | Cooper | |
| 5,697,976 A | 12/1997 | Chesterfield et al. | |
| 5,702,462 A | 12/1997 | Oberlander | |
| 5,716,376 A | 2/1998 | Roby et al. | |
| 5,722,991 A | 3/1998 | Colligan | |
| 5,887,594 A | 3/1999 | LoCicero, III | |
| 5,897,572 A | 4/1999 | Schulsinger et al. | |
| 5,931,855 A | 8/1999 | Buncke | |
| 5,964,783 A | 10/1999 | Grafton et al. | |
| 5,972,024 A | 10/1999 | Northrup et al. | |
| 5,984,933 A | 11/1999 | Yoon | |
| 6,012,216 A | 1/2000 | Esteves et al. | |
| 6,027,523 A | 2/2000 | Schmieding | |
| 6,056,778 A | 5/2000 | Grafton et al. | |
| 6,083,244 A | 7/2000 | Lubbers et al. | |

| | | | |
|---|---|---|---|
| 6,102,947 A | 8/2000 | Gordon | |
| 6,163,948 A | 12/2000 | Esteves et al. | |
| 6,241,747 B1 | 6/2001 | Ruff | |
| 6,251,143 B1 | 6/2001 | Schwartz et al. | |
| 6,270,517 B1 | 8/2001 | Brotz | |
| 6,433,962 B2 | 8/2002 | Solomon et al. | |
| 6,443,962 B1 | 9/2002 | Gaber | |
| 6,478,809 B1 | 11/2002 | Brotz | |
| RE37,963 E | 1/2003 | Thal | |
| 6,599,310 B2 | 7/2003 | Leung et al. | |
| 6,645,226 B1 | 11/2003 | Jacobs et al. | |
| 6,773,450 B2 | 8/2004 | Leung et al. | |
| 6,848,152 B2 * | 2/2005 | Genova et al. | 29/7.1 |
| 6,905,484 B2 * | 6/2005 | Buckman et al. | 604/174 |
| 7,056,331 B2 | 6/2006 | Kaplan et al. | |
| 2003/0014077 A1 | 1/2003 | Leung et al. | |
| 2003/0149447 A1 | 8/2003 | Morency et al. | |
| 2004/0030354 A1 | 2/2004 | Leung et al. | |
| 2004/0060410 A1 | 4/2004 | Leung et al. | |
| 2004/0088003 A1 | 5/2004 | Leung et al. | |
| 2004/0106949 A1 | 6/2004 | Cohn et al. | |
| 2004/0193191 A1 | 9/2004 | Starkson et al. | |
| 2005/0203576 A1 | 9/2005 | Sulamanidze et al. | |
| 2007/0005109 A1 | 1/2007 | Popadiuk et al. | |
| 2007/0224237 A1 | 9/2007 | Hwang et al. | |

FOREIGN PATENT DOCUMENTS

| | | |
|---|---|---|
| CN | 2640420 Y | 9/2004 |
| DE | 1 180 800 | 6/1970 |
| DE | 1 810 800 | 6/1970 |
| DE | 1810800 | 6/1970 |
| DE | 4302895 | 8/1994 |
| DE | 19618891 C1 | 4/1997 |
| DE | 198 33 703 | 2/2000 |
| DE | 198 33 703 A | 2/2000 |
| DE | 19833703 | 2/2000 |
| EP | 0428253 B1 | 5/1991 |
| EP | 0 576 337 A1 | 12/1993 |
| EP | 0576337 | 12/1993 |
| EP | 0576337 B1 | 5/1997 |
| EP | 0612504 | 11/1997 |
| EP | 0 826 337 | 3/1998 |
| EP | 0 826 337 A | 3/1998 |
| EP | 0 839 499 | 5/1998 |
| EP | 0 839 499 A | 5/1998 |
| EP | 0913123 | 5/1999 |
| EP | 1 075 843 A1 | 2/2001 |
| EP | 1075843 | 2/2001 |
| FR | 2619129 | 2/1989 |
| FR | 2693108 | 6/1992 |
| FR | 9208059 | 12/1993 |
| FR | 2693108 | 1/1994 |
| FR | 9208059 | 3/1997 |
| GB | 1091282 | 11/1967 |
| GB | 1 428 560 | 3/1976 |
| GB | 1506362 | 4/1978 |
| JP | 54116419 A | 9/1979 |
| JP | 01113091 A | 5/1989 |
| JP | 10085225 | 4/1998 |
| JP | 11332828 | 12/1999 |
| JP | 11332828 A * | 12/1999 |
| NZ | 501224 | 1/2002 |
| NZ | 531262 | 12/2005 |
| RU | 2139690 | 10/1999 |
| RU | 2139690 C1 | 10/1999 |
| SU | 1745214 | 7/1992 |
| SU | 1752358 | 8/1992 |
| WO | 96-06565 | 3/1996 |
| WO | WO 98/52473 | 11/1998 |
| WO | WO/9852473 | 11/1998 |
| WO | WO 99/21488 | 5/1999 |
| WO | WO 00/51658 | 9/2000 |
| WO | WO/03001785 | 1/2003 |
| WO | WO 03/017850 | 3/2003 |
| WO | WO 03/017850 A | 3/2003 |
| WO | WO 03/017850 A2 | 3/2003 |
| WO | WO 03/045255 | 6/2003 |
| WO | WO 03/103972 A1 | 12/2003 |
| WO | WO /03103972 A1 | 12/2003 |
| WO | WO 2004/030520 | 4/2004 |
| WO | WO 2004/030704 | 4/2004 |
| WO | WO 2004/030705 | 4/2004 |
| WO | 2006-061868 | 6/2006 |
| WO | 2007-133103 | 11/2007 |

OTHER PUBLICATIONS

Sulamanidze, M.D., M.A.; Shiffman, M.D., J.D., M.A.; Paikidze, M.D., T.G.; Sulamanidze M.D., G.M.; Gavasheli, M.D., L.G., "Facial Lifting with APTOS Threads"; *International Journal of Cosmetic Surgery and Aesthetic Dermatology*, No. 4 2001, pp. 1-8.

McKenzie, A.R.; "An Experimental Multiple Barbed Suture for the Long Flexor Tendons of the Palm and Fingers", The Journal of Bone and Joint Surgery, vol. 49B, No. 3, Aug. 1967, pp. 440-447.

"Drilled End Surgical Needles", B.G. Sulzle, Inc., Syracuse, New York, Jul. 2002.

Sulamanidze, M.A., et al.; "Facial Lifting with "Aptos" Threads", Jul. 18, 2001, www.fonendo.com, pp. 1-6.

Dattilo, Jr., Philip P., et al.; "Medical Textiles: Application of an Absorbable Barbed Bi-directional Surgical Suture", Journal of Textile and Apparel, Technology and Management, vol. 2, Issue 2, Spring 2002; RTP, North Carolina.

"Up Lifting (Aptos Threads)", http://www.ccpr.com.br/upl-l.htm, Aug. 19, 2002, pp. 1-2.

Han, Hougtao, et al.; "Mating and Piercing Micromechanical Structures for Surface Bonding Applications" Micro Electro Mechanical Systems, (MEMS-91), Nara, Japan, Jan. 31-Feb. 2, 1991. CH2957-9/91, pp. 253-258, 1991.

Buncke, Jr., H. J., et al.; "The Suture Repair of One-Millimeter Vessels" Micro-Vascular Surgery; Report of First Conference, Oct. 6-7 1966. pp. 24-35 (esp. p. 34), 1966; USA.

Sulamanidze, M.A., et al.; "Removal of Facial Soft Tissue Ptosis With Special Threads" Dermatol Surg 2002, 28, pp. 367-371; Blackwell Publishing, Inc.

Declaration of Dr. Gregory L. Ruff, Dated Aug. 19, 2005, 8 pages, with Exhibits A-E.

Semenov, G.M. "Surgical Suture", Jun. 23, 1905, Piter, pp. 12-13, 92-98.

Boenisch, U.W. "Pull-out strength and stiffness of meniscal repair using absorbable arrows or Ti-Cron vertical and horizontal loop sutures" Sep.-Oct. 1999, Am J. Sports med. 27(5):626-31 (Abstract).

Sulamanidze M.A., et al.; Facial Lifting with APTOS Threads; International Journal of Cosmetic Surgery and Aesthetic Dermatology; pp. 1-8.

Philip P. Datillo Jr. et al.; Tissue Holding Performance of Knotless Absorbable Sutures; Society for Biomaterials 29th Annual Meeting Transactions (2003); p. 101.

A. Schmid et al.; The outspreading anchor cord. A material for arthroscopic suturing of a fresh anterior cruciate ligament rupture.

* cited by examiner

APPARATUS AND METHOD FOR FORMING BARBS ON A SUTURE

BACKGROUND OF THE INVENTION

1. Field of the Invention

The invention relates to an apparatus for forming barbs on a filament and the component parts of the apparatus.

2. Description of the Prior Art

In the prior art, it is well known that surgical and traumatic wounds are typically closed with a filament introduced into the tissue by a needle attached to one end. Closure of the wound and holding tissues together supports healing and re-growth. What is typically used for this procedure is known as a suture.

A barbed suture is a one-way suture which allows passage of a needle-drawn suture in one direction through tissue, but not in the opposite direction. A barbed suture is generally an elongated body having a pointed leading end and a plurality of axially and circumferentially spaced barbs on the exterior surface of the elongated body.

In closing a wound with a barbed suture, the suture is passed through tissue at each of the opposed sides of a wound. Suture pairs are formed in which trailing ends of sutures are positioned generally in alignment at opposite sides of the wound. On insertion of each suture, the needle is pushed to extend out of the tissue at a point laterally remote from the wound, then the needle is pulled out to draw the suture to the desired position. The suture may then be severed from the needle or inserted again. (Note that methods of using barbed sutures are disclosed in copending U.S. patent application Ser. No. 09/943,733, "Method of Forming Barbs on a Suture and Apparatus for Performing Same," the disclosures of which is incorporated herein by reference.) These methods are also described in International Patent Application, PCT/US02/27525. One advantage of using barbed sutures is that there is an ability to put tension in the tissue with the result of less slippage of the suture in the wound. Another advantage is that barbed sutures do not require tying as in prior art suturing methods. The number of suture pairs is selected in accordance with the size of the wound and the strength required to hold the wound closed. Although tissue anchoring is easier with a very pointed barb and a relatively skinny tip, better tissue holding results are obtained with a fuller tip barb.

In some circumstances of tissue repair, a random configuration of barbs on the exterior of the suture is preferred. With as many barb angles as possible, superior wound holding may be achieved. However, in other circumstances where the wound or tissue repair needed is small, a small suture is preferable. A thin suture may require a reduced number of barbs on the exterior of the suture.

In other circumstances the use of two-way barbed suture is preferable. A two-way barbed suture is one that has barbs permitting passing of the suture in one direction over a portion of the suture and barbs permitting passing of the suture in a second direction over another portion of the suture. Such an arrangement permits the passage of the suture through the tissue until the second set of barbs abut the tissue. Because the first set of barbs cannot be passed backward through the tissue and the second set of barbs cannot pass through the tissue, a firm closing stitch can be easily accomplished.

Additional methods of cutting barbs on a suture filament have been proposed (see e.g. U.S. Pat. No. 5,931,855 to Buncke).

It is seen from the foregoing that there is a need for an apparatus for cutting barbs in two directions on the exterior of sutures with a minimum of difficulty and in a precise, reliable and relatively economic fashion so as to allow for the wide spread commercialization of such sutures. Such an apparatus should also be able to vary the size of the barbs, their location and depth to allow for variation thereof and virtuality of their application. The apparatus should be able to cut a plurality of barbs positioned depending on the number of barbs needed. The configuration of the apparatus should also be variable depending upon, among other things, the type barbs being cut and the type of filament material, both of which relate to the type tissue being repaired. The apparatus should further be comprised of a series of components each of which facilitates the cutting of the barbs, these components being variable in configuration depending upon the desired features of the barbs to be cut.

OBJECTS OF THE INVENTION

It is therefore an object of the present invention to provide an apparatus for cutting barbs into a filament. The apparatus includes a filament supply, an in-feed collet for holding one end of a filament threaded therethrough, and an out-feed collet for holding a second end of a filament threaded therethrough. The apparatus also includes a holder positioned between the in-feed and out-feed collets for holding a filament suspended between them and a cutting assembly for cutting barbs in the filament tensioned between the in-feed and out feed collets. The apparatus may further include a tensioner for tensioning the filament held between the in-feed and out-feed collets, and a cutter for cutting a filament to a desired length to form a suture after barbs have been cut into the filament.

The cutting assembly may be formed of a first directional feed motor for moving a first cutter, a second directional feed motor for moving a second cutter, and a third directional feed motor for moving a grasping tool. The first and second cutters cut barbs into a filament and the grasping tool advances the filament after cutting of the barbs. The directional feed motors may comprise a series of feed motors that permit the independent motion of the cutters along the vertical, longitudinal, and perpendicular directions relative to the filament. The directional feed motors may move in varying degrees of motion relative to the other directional feed motors to enable the barbs to be cut in various lengths, depths, and shapes.

The present invention also relates to an apparatus for cutting barbs into sutures having a first directional feed motor for moving a first cutter, a second directional feed motor for moving a second cutter, and a third directional feed motor for moving a grasping tool, wherein the first and second cutters cut barbs into a filament and the grasping tool advances the filament after cutting of the barbs. The apparatus may also include a severing blade for severing the filament after advancement to form a suture.

The present invention further relates to a holder for securing a suture in preparation for the cutting of barbs. The holder includes a bed, having a channel arranged in the bed, and a plurality of orifices arranged along the channel. Each orifice has a first end exposed in the channel and a second end connected to a suction. A suction applied to the second end creates a vacuum for securing a suture placed over the orifices.

Still further, the present invention relates to a collet for holding a suture in place relative to its longitudinal axis during the cutting of barbs. The collet includes a chuck support and a chuck with a variably adjustable aperture. The chuck includes a plurality of jaws, whereby movement of the jaws adjusts the aperture of the chuck. The chuck may have two, three, or more jaws. The chuck may be configured to impart a variable filament retention force depending upon the characteristics of the filament be used. This variable filament retention force prevents damage to the filament. In a two jawed configuration, it may be preferable that a face of the jaw contacting the suture be concave. The chuck may further be rotatable about a longitudinal axis of a suture to impart twist to the suture. It may be preferable that the collet rotate in both a first and second direction. Further, the collet may be formed of materials that do not impart contaminants onto the filament.

Further still, the present invention relates to an apparatus for cutting barbs into sutures having a suture material supply, for feeding suture material to at least one collet and a tensioner. The tensioner includes at least one fixed pulley and at least one movable biased pulley, wherein the movable biased pulley imparts a force on the suture material tensioning a section of suture material held by the at least one collet. The tensioner may be adjustable to provide a variable but uniform amount of tension to a variety of filament types.

Yet another aspect of the present invention relates to an apparatus for cutting barbs into sutures having at least one collet and at least one biased tensioner. The biased tensioner allows the collet to move in a first direction as a suture held in a chuck housed in the collet is twisted. The biased tensioner moves the collet in a second direction as the suture is untwisted. The movement of the collet insures that the suture receives no more than a specified tension.

The present invention still further relates to a cutter for use in an apparatus for cutting barbs into sutures. The cutter includes a first edge which has a sharply honed edge for cutting a barb into a suture to a specified depth and in a specified direction. The cutter may also include a second edge which is blunted and roughened to impart a roughened texture to a surface of the barb cut into the suture, e.g. a serrated or corrugated underside. Alternatively, cutting blades with ends that are arcuate can create an arcuate shape at the base of the barb so as to reduce the sheering stress focused at the vertex of the barb.

In a further embodiment, the present invention relates to an apparatus for cutting barbs into a suture having a filament supply, at least one collet for holding a filament, a cutting bed for resting a filament thereon, and a cutting assembly for cutting barbs in the filament.

In yet a further embodiment the present invention relates to a method of forming a barbed suture comprising the steps of first threading a filament from a filament supply through a filament tensioner and through a first and second collet. Next the first and second collets are closed, and at least one of them is rotated in a first direction to twist the filament. Barbs are then cut into the filament. The filament is then untwisted and the collets are opened. The filament is then advanced with the use of a grasping tool, and the collets are again closed. Then the filament is severed to form a suture.

These and other objects and characteristics of the present invention will become apparent from the further disclosure to be made in the detailed description given below.

DETAILED DESCRIPTION OF THE PREFERRED EMBODIMENTS

The present invention relates to an apparatus for forming barbs on a suture filament. Various components of the apparatus are also described each of which represents a novel aspect of the present invention.

Figure 1:
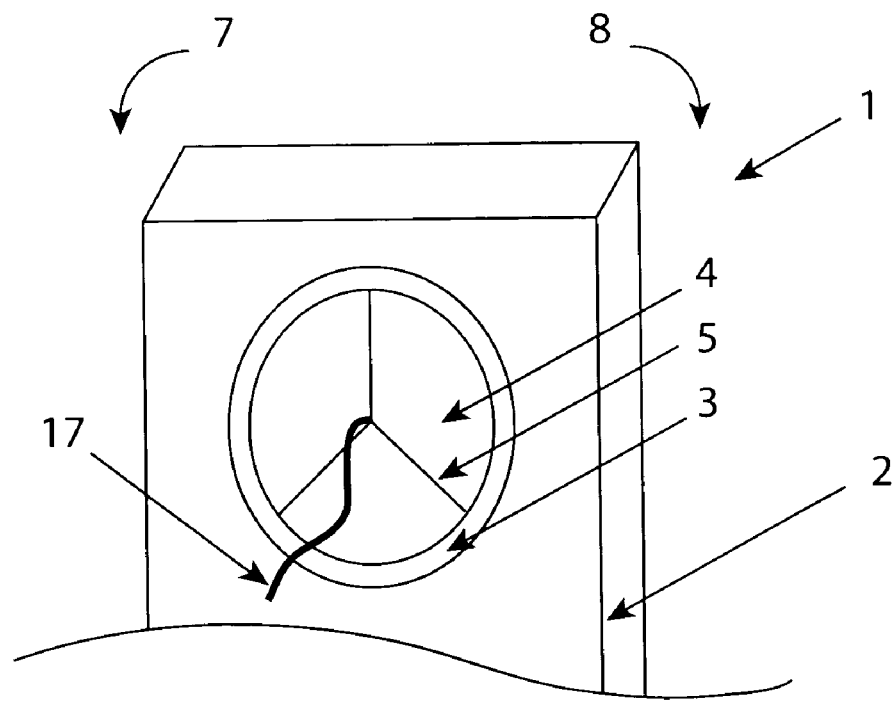
FIG. 1, depicts a perspective view of a collet with a three jaws.
Figure 5:
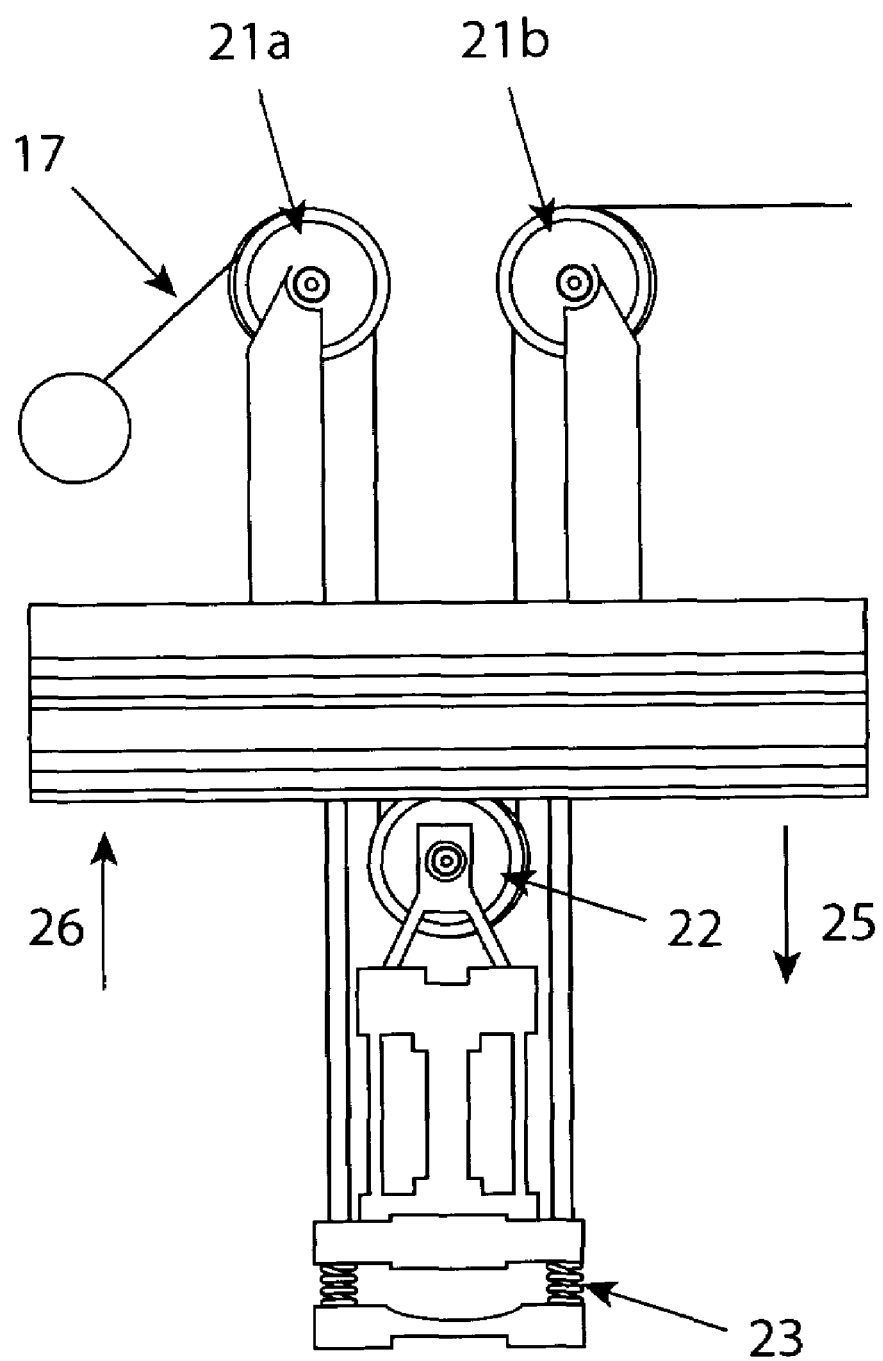
FIG. 5, depicts a perspective view of a filament tensioner.
Figure 10:
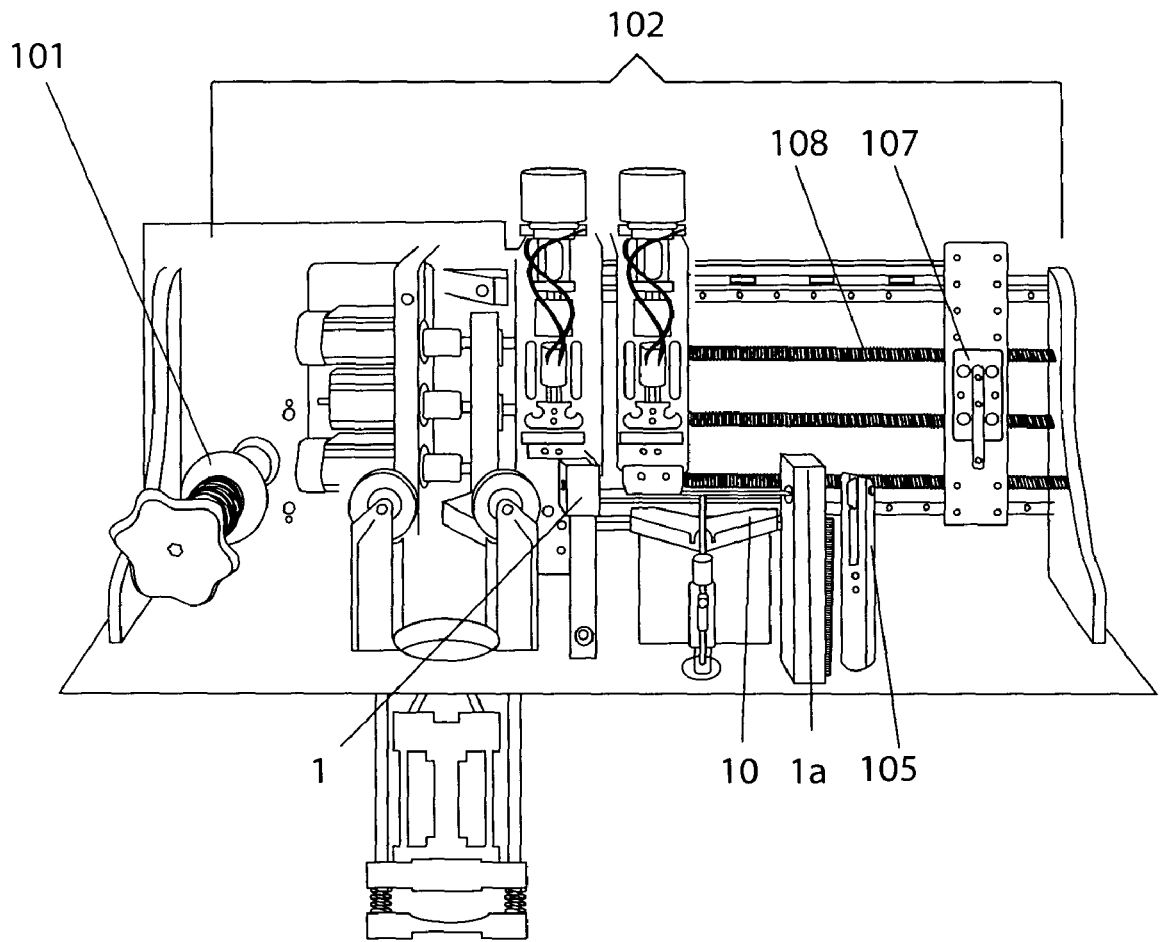
FIG. 10, depicts a perspective view of the apparatus.

The apparatus as shown in FIG. 10 comprises a filament supply 101. The filament supply is preferably spool as shown in FIG. 10. The filament supply 101 may optionally be motor operated. A filament 17 from the filament supply 101 is threaded through a tensioner 20, as show in FIG. 5. From the tensioner 20, the filament is threaded to an in-feed collet 1. The filament is then threaded through an out-feed collet 1a, and tensioned by the tensioner 20. The tensioned filament is held between the closed in-feed and out-feed collets 1, 1a. Between the in-feed and out-feed collets 1 and 1a, the filament is placed upon a holder or cutting bed 10, which supports the filament during the cutting process. The filament is held firmly by chuck, 3, of the in-feed and out-feed collets when closed as shown in FIG. 1. The cutting assembly 102 is then arranged to cut the barbs.

The cutting assembly 102 comprises a plurality of directional feed motors 103 that operate drive screws 108 for moving the cutters 106 longitudinally along the filament. Preferably the directional feed motors 103 are stepper motors which can accurately control the location of the cutting heads 106, shown in FIG. 11. The cutting assembly 102 also comprises a cutting motor 109 for articulating the cutters 106 and a height adjusting motor 110. The various motors permit the independent motion of the cutters along the vertical, longitudinal, and perpendicular directions relative to the filament. The motors may further move in varying degrees of motion relative to the other motors to enable the barbs to be cut in various lengths, depths, and shapes.

Figure 11:
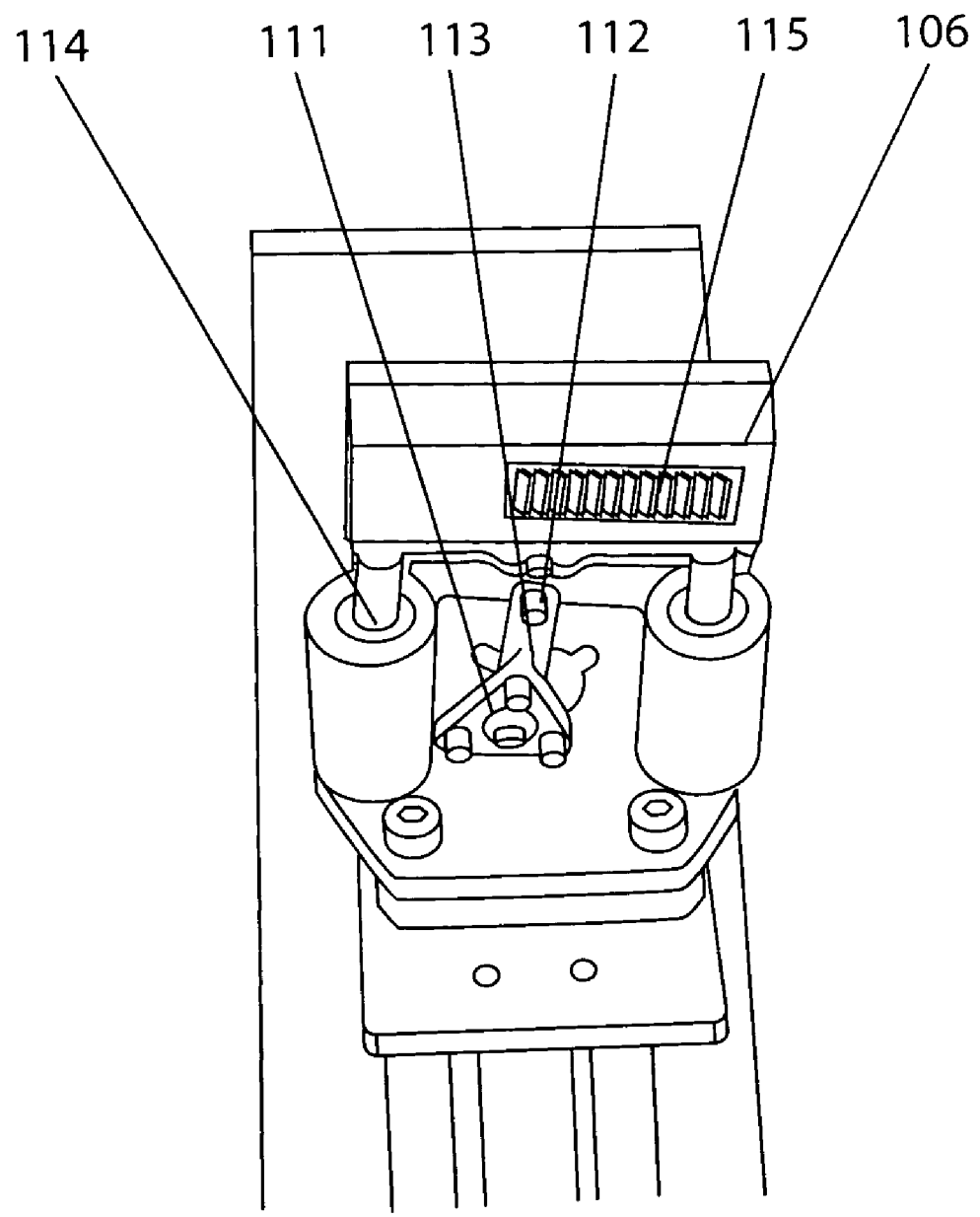
FIG. 11, depicts an underside perspective view of the cutter.

In the preferred embodiment the cutters 106 are oscillated to effect a cutting motion. This may be performed as shown in FIG. 11, through the use of an offset coupling 111 connected to the shaft of the cutting motor 109 and a pin 112 attached to the cutters 106. As the cutting motor 109 turns, the offset coupling 111 forces a link 113 to impart a force on the cutters 106. This force propels the cutters in a direction substantially perpendicular to the longitudinal direction of the filament. To ensure that only linear motion is imparted on the cutter 106, sliding rams 114 are used. Sliding rams 114, when used in conjunction with the pin 112, and the offset coupling 111 assist in transferring any rotational motion imparted on the cutter by the cutter motor 109 to linear motion and prevent any rotational force to be applied to the cutters 106. In effect the cutters 106 saw into the filament.

The height adjusting motor 110 insures that the cutters 106 are properly positioned over the filaments for cutting. The height adjusting motor 110 also lowers the cutters 106 during the cutting of the barbs to create a barb of a desired depth into the filament. Again, due to the precise nature of the movements, a stepper motor is used in the preferred embodiment.

In operation, a first cutter 106 is operated by a first directional feed motor 103 that moves the first cutter 106 in a first direction along the longitudinal axis of the filament. A second directional feed motor 103 moves a second cutter 106 in an opposite direction along the longitudinal axis of the filament. And a third directional feed motor 103 controls the movement of the grasping tool 107.

During the cutting of barbs, the directional feed motors 103 may move the cutters 106 linearly along the filament to force the barb away from the filament which gives the barb better holding power when in use.

Figure 12:
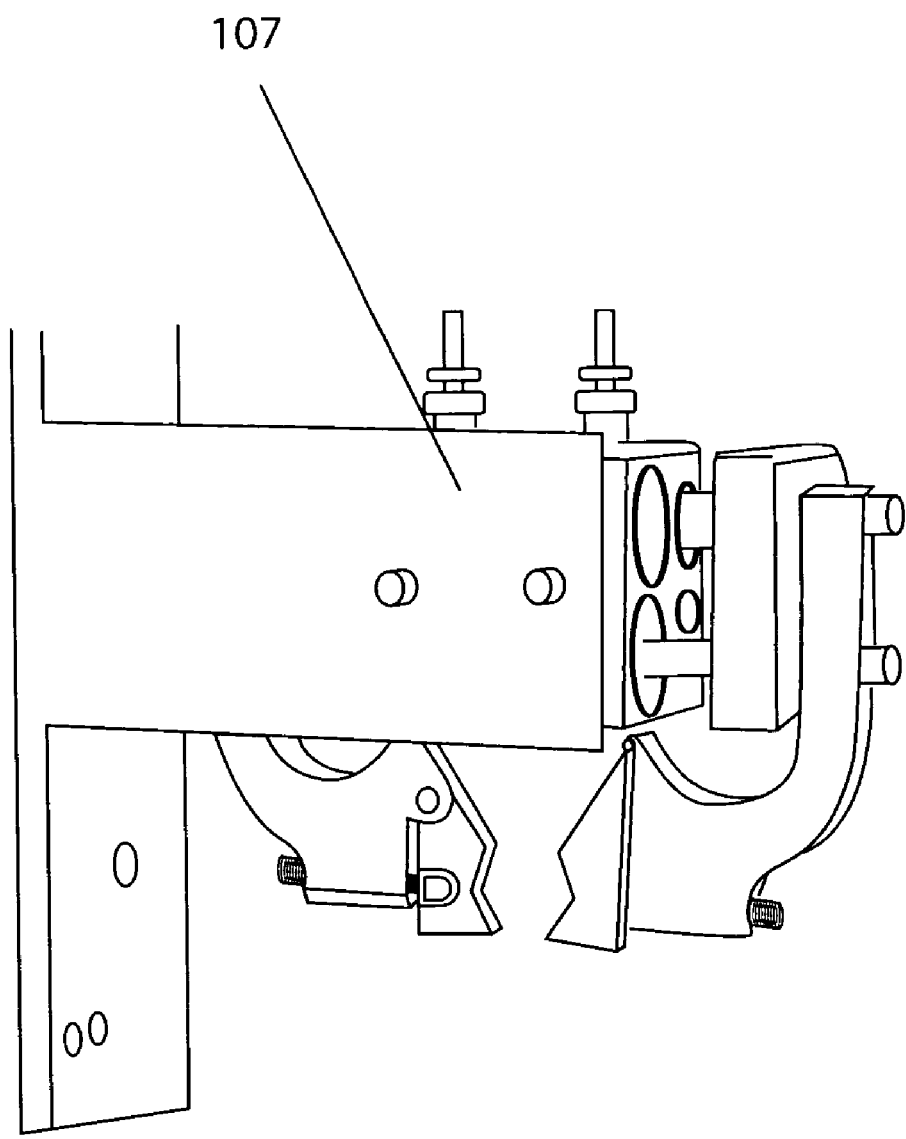
FIG. 12, depicts a close-up perspective view of the grasping tool.
Figure 13:
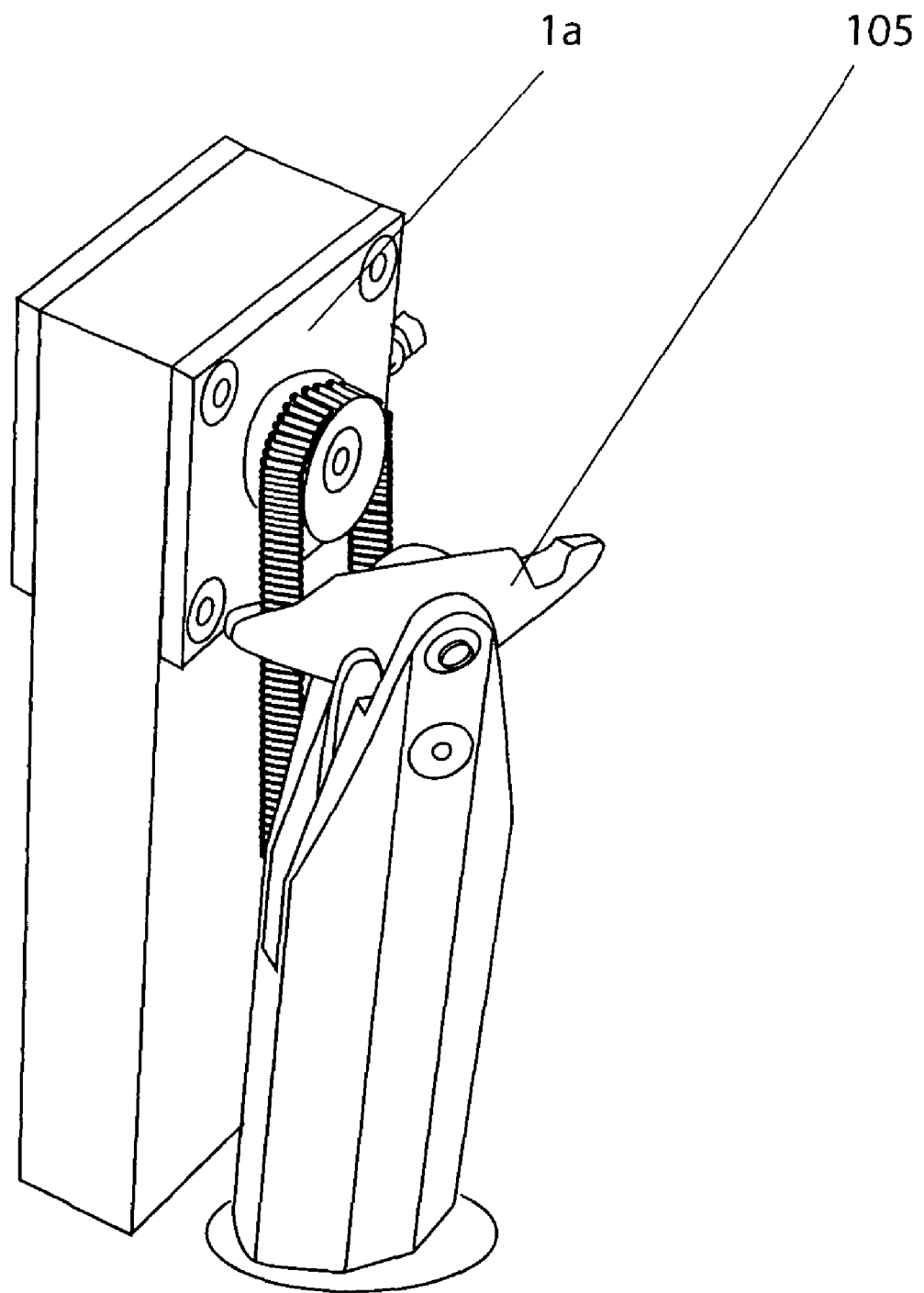
FIG. 13, depicts a close-up perspective view of the out-feed collet and the cutter.
Figure 14:
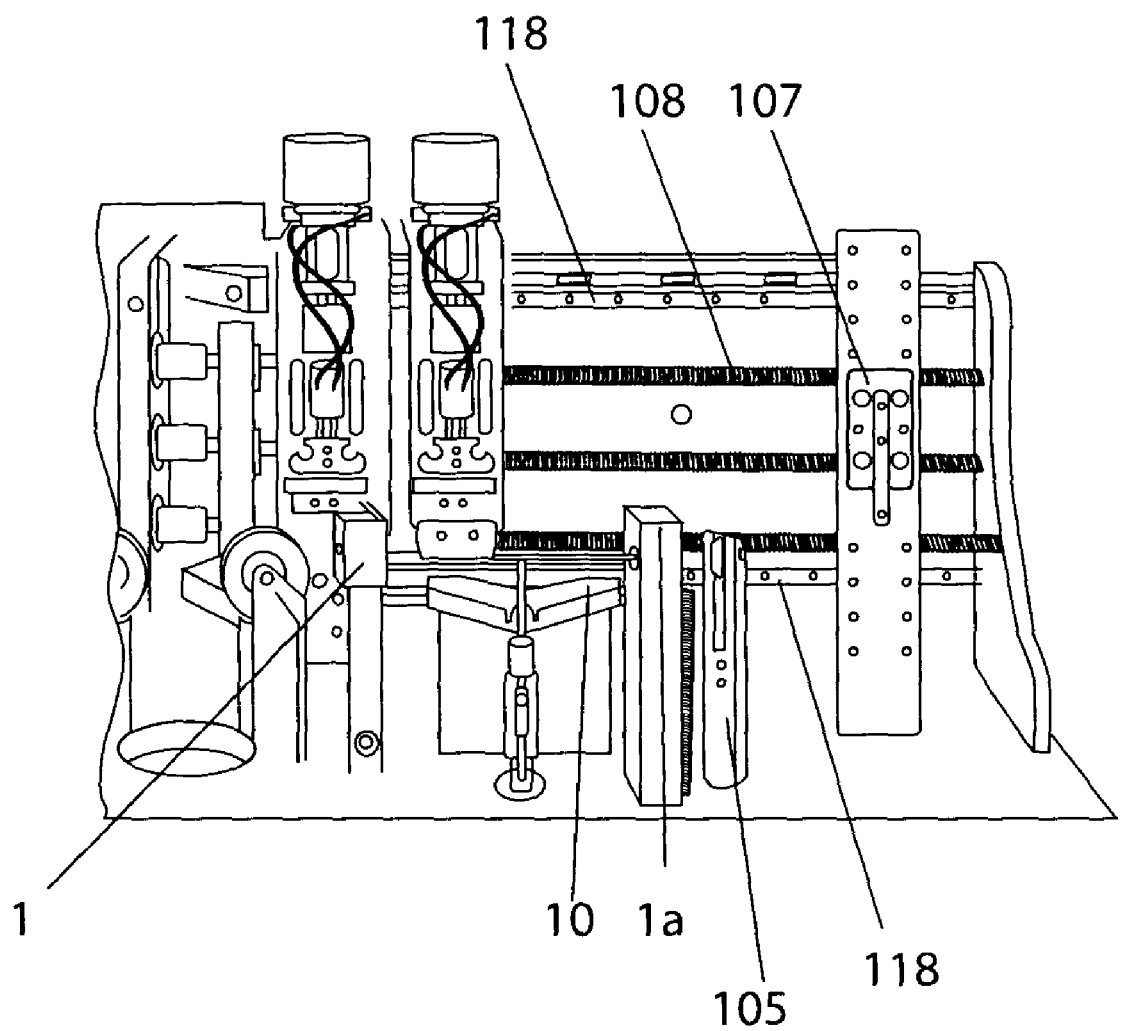
FIG. 14, depicts a close up view of the cutting assembly, and the in-feed and out-feed collets.
Figure 15:
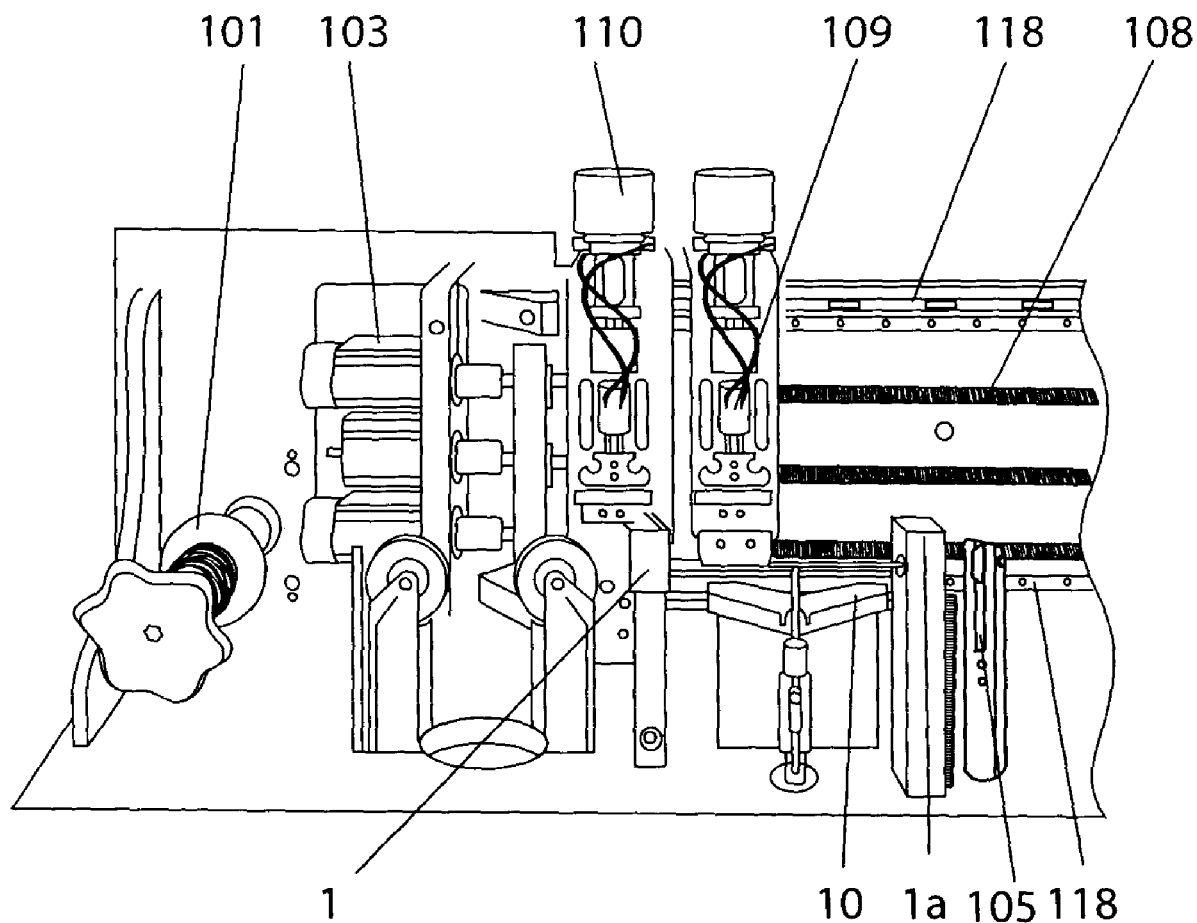
FIG. 15, depicts a close up view of the apparatus.

After the barbs are cut onto the filament, the filament is advanced, so that the next suture may have barbs cut therein. The advancement method may comprise a simple motor operated drum and spool (not shown) as the filament supply, or preferably a grasping tool 107 operated by a directional feed motor 103, and driven by a drive screw 108 as seen in FIGS. 12 and 14. The grasping tool 107 grasps an end of the filament that protrudes from the out-feed collet 1*a*. The grasping tool 107 is then advanced away from the out-feed collet 1a by the directional feed motor 103. Upon reaching a specified distance the out-feed collet 1*a* closes and a severing blade 105 cuts the filament to produce the suture.

The opening and closing of the grasping tool may be performed in a variety of ways including, but not limited to electromagnetic relays, pneumatic actuation, and hydraulic actuation.

The sutures, once cut, may be packaged for later application of needles or hooks or a hook attachment device (not shown) may immediately place hooks on the suture before packaging. In the latter scenario, a hook is attached to the end of the filament that protrudes from the out feed collet 1*a* while the barbs are being cut into the filament. After the barbs are cut, the grasping tool 107 draws the filament out to be cut to length and the second hook is applied after cutting. The grasping tool 107 then releases the completed suture for later packaging.

It is preferable that the cutting of the barbs occur in two opposite directions on the filament, as the barbs are intended to allow movement of the suture in only one direction. Having two opposing sections of barbs, the surgeon or medical personnel placing the suture can insure that the suture will not come undone once placed. Accordingly, the present invention allows for cutting of barbs in two opposing longitudinal directions of the filament, without the need to reverse the filament or the cutting blades.

Typically, the cutting assembly 102 has two cutters 106, one for cutting barbs facing a first direction and one for cutting barbs facing a second direction. In instances where a long section of barbs is desired, the cutters 106 may be moved by the directional feed motors 103 after cutting the first set of barbs to initiate a second or more sets of barbs to create a seamless transition from section to section of the barbs. In such instances it may become necessary to cut two or more sections of barbs in a first direction, advance the filament, and then cut two or more sections of barbs in the second direction.

The cutter 106 may be formed of a plurality of cutting blades 115 as shown in FIG. 11. While in the preferred embodiment they resemble those described with respect to FIG. 6 other cutting blades may also be used.

The cutters 106 and their operational motors 109 and 110 ride on bearing tracks 118 which limit the friction that must be overcome by the directional feed motor 103 to move the cutter 106. In a preferred embodiment, the cutter is mounted on two bearing tracks 118 connected by a plate 116. A follower 117 is mounted on the plate 116, the drive screw 108 is threaded through the follower 117. The follower 117 has internal threads matching those of the drive screw 108. The directional feed motor 103 in turn drives the drive screw 108, which in turn acts upon the follower 117 and the attached plate 116 to position the cutter 106. The directional feeds 103 are preferably stepper motors although other motors may be used. The stepper motor allows for finite control of the directional feed necessary to achieve the desired finish to the suture. By use of the stepper motor the exact position of the cutters 106 relative to the filament 17 can be accurately and repeatably ascertained. The cutters 106 can be manipulated by the barb cutting apparatus to enable a wide variety of shapes of barbs to be cut into the filament 17.

Figure 3:
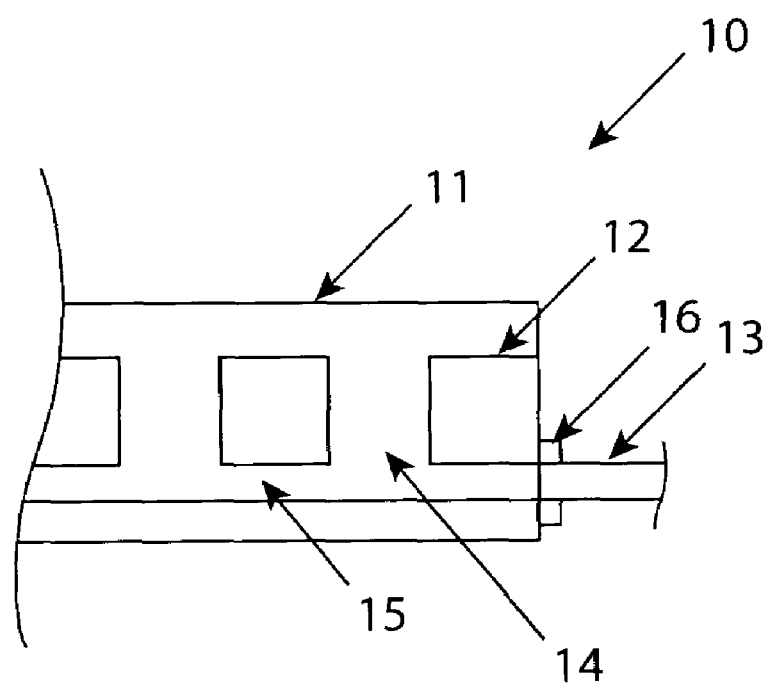
FIG. 3, depicts a profile view of a filament holder.
Figure 4:
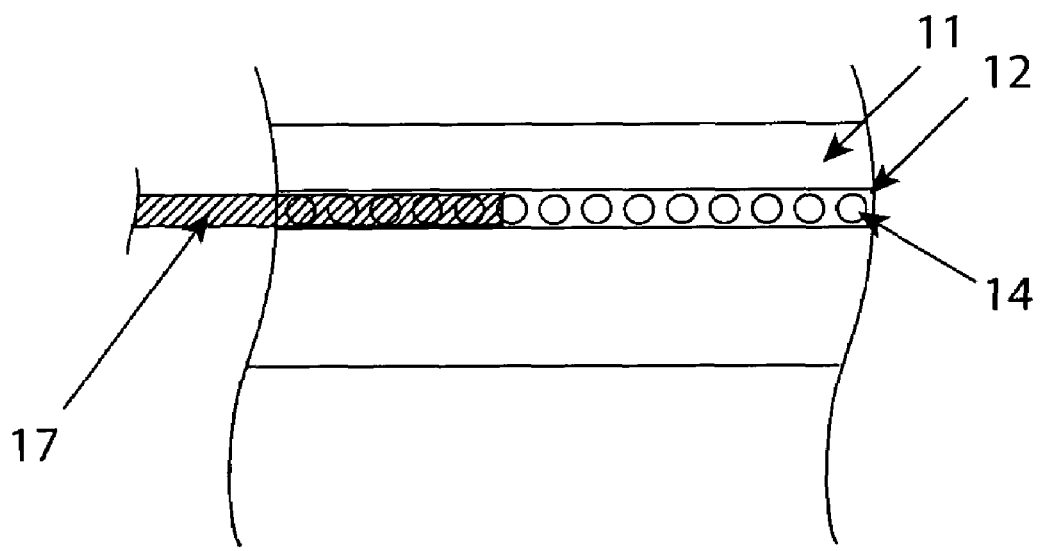
FIG. 4, depicts a top view of a filament holder.

In FIGS. 3 and 4, a holder 10 for securing a filament in accordance with another aspect of the invention is shown. The holder 10, secures the suture from lateral movement while barbs are cut into the filament. The holder provides a uniform profile for the cutting step and spreads the retention force along the length of the filament 17. The spreading of the retention force avoids acute stresses that can damage the filament 17 during the cutting process. The holder is preferably comprised of a bed 11, and the bed is preferably made of steel or other machinable metal. Alternatively, the bed could be made of plastic, glass, ceramic or any other material suitable for the purpose. The bed surface is preferably machined flat and operates as a working surface for the cutting assembly 102. The bed has a channel 12 machined into the exposed surface of the bed. The diameter of channel 12 is preferably the same as or slightly greater than the diameter of the suture material to be cut. The depth of channel 12 is preferably shallower that the diameter of the filament into which barbs are to be cut. Along the bottom of the channel 12 are a series of orifices 14. Each orifice is preferably connected in common to a bore 15. The bore 15 is connected to a vacuum or suction means 13 for drawing a vacuum on the bore 15 and the orifices 14. The vacuum means 13 for drawing a vacuum on the bore 15 and the orifices may simply be a tube or pipe connected to a vacuum source as shown in FIG. 3. Such a tube may require a fastener 16 for connection of the vacuum means to the holder.

In operation, filament 17 is drawn through channel 12 of bed 11 of the holder 10 substantially covering the orifices 14. Suction is then applied to the vacuum means 13. The vacuum produced by the suction translates to the orifices 14, which in turn holds the filament 17 rigidly in place. Once the filament is held rigidly in place a cutting operation can be commenced to cut barbs into the filament 17.

Figure 2:
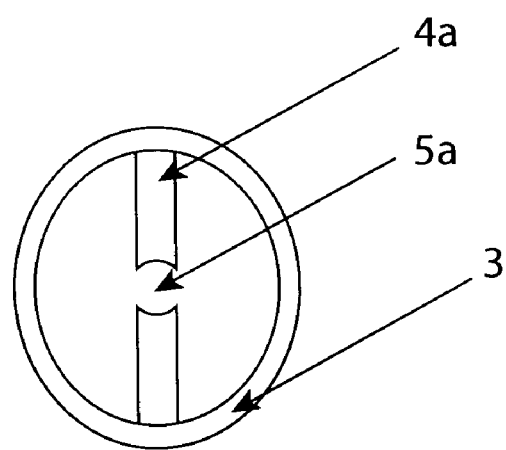
FIG. 2, depicts a front view of a chuck with two jaws.

A collet 1, in accordance with another aspect of the invention is shown in FIG. 1. The collet 1 holds a filament that has been threaded therethrough. The collet 1 secures the filament firmly without damaging the filament even during twisting. The collet 1 is comprised of a support 2 and a chuck 3. Chuck 3 has a plurality of articulating jaws 4, which may be opened and closed to facilitate the passing of a filament through the collet 1. The jaws 4 close to hold a filament. The jaws 4 are preferably finely machined so that they can close tightly around the filament without damaging it. The chuck 3 may house two jaws positioned, for example, 180° apart as shown in FIG. 2, or three jaws positioned approximately 120° apart as shown in FIG. 1, or more.

In the three jaw configuration as shown in FIG. 1 it is preferable that each jaw have a substantially flat gripping surface 5 which enables all three jaws 4 to simultaneously grip the filament 17. In the two-jaw configuration it is preferable that each jaw 4a have a concave gripping surface 5a. The concave gripping surface is sufficiently shallow to allow the jaws 4a to firmly hold the filament. The positioning and configuration insures that the jaws 4a apply even pressure to the filament and have good holding power without damaging the filament 17. Additionally, the jaws may be formed of a material that prevents contamination of the filament 17.

The jaws 4 and 4a are preferably pneumatically operated for closing the jaws and spring biased to open the jaws, in a normally open jaw configuration. Alternatively, a normally closed jaw configuration could be utilized where the pneumatic pressure opens the jaws and the spring force closes them. Additionally, one skilled in the art would appreciate that the jaws could be opened and closed by alternative means. For example the jaws could be opened and closed by electromechanical, hydraulic, or simple mechanical threading means as in a drill bit chuck.

The chuck 3 of the collet 1 is preferably rotatable. Rotation of the chuck 3 facilitates the imparting of twist to a filament held by the jaws 4 or 4a. By imparting twist, the cutting assembly 102 is able to cut in a single pass barbs on the filament that are offset from one another when the filament is untwisted. For further discussion of the practice of twisting the filament before cutting barbs see U.S. patent application Ser. No. 09/943,733, the disclosure of which is incorporated herein by reference. The rotation of the collet is preferably actuated by an electrical motor. However pneumatic, or hydraulic means could also be employed without departing from the scope of the present invention.

Preferably the barb cutting apparatus comprises two collets an in-feed collet 1, and an out-feed collet 1a. Either one or both of these collets may be rotatable. However it is preferable that at least the out feed collet is rotatable. Further, it is preferable that the out-feed collet 1a be rotatable in both a first direction 7 and second direction 8. This facilitates both the imparting of twist on a filament and the removing of twist from the filament. However, there may exist applications, and filament fibers for which imparting and maintaining twist is preferable for storage or other applications. In such applications the filament can be twisted and untwisted as desired without departing from the scope of the present invention.

The present invention further relates to a tensioner 20 for tensioning a filament 17. The tensioner 20 comprises pulleys 21 and 22. The pulleys consist of stationary pulleys 21a and 21b and movable pulley 22. The tensioner 20 ensures that the filament 17 is constantly under a relatively uniform tension throughout the advancement, twisting and barb cutting steps.

The filament is preferably run over a first stationary pulley 21a, under a movable pulley 22, and then over a second stationary pulley 21b. In a preferred embodiment, a springs 23 act as limiting devices stopping the movement of the moveable pulley 22 in a first direction 25. The movable pulley is weighted, this weight tensions the filament as it is drawn through the collets by the gripping tool 107. The movement of the filament by the gripping tool 107 causes the movable pulley 22 to move in a second direction 26. Accordingly, the length of travel of the movable pulley 22 is approximately equal to maximum length of a suture. Upon stopping movement in the second direction 26, the filament supply 101 slowly rotates to allow the filament to be pulled away from the filament supply 101 and in the direction of the stationary pulley 21a. This allows the movable pulley 22 to move in the first direction 25 until contacting the springs 22. The filament supply 101 is most preferable operated by a stepper motor which can gradually advance the filament until the movable pulley 22 contacts the springs 23. Sensors may be added to stop the motor when the movable pulley reaches a predetermined position.

In use, the tensioner 20 ensures that filament 17 which spans from an in-feed collet to an out-feed collet is properly tensioned. Tensioning is necessary to ensure that the filament 17 can be properly twisted and subsequently have barbs cut therein. Tensioning of the filament 26 further assists in preventing the filament from moving during the cutting process and insures proper alignment of the filament 17. The initiation of the supply of the filament by the rotation of the filament supply 101 is not begun until after the in feed collet 1 has closed on the filament. This insures that there is always tension on the filament.

Figure 7:
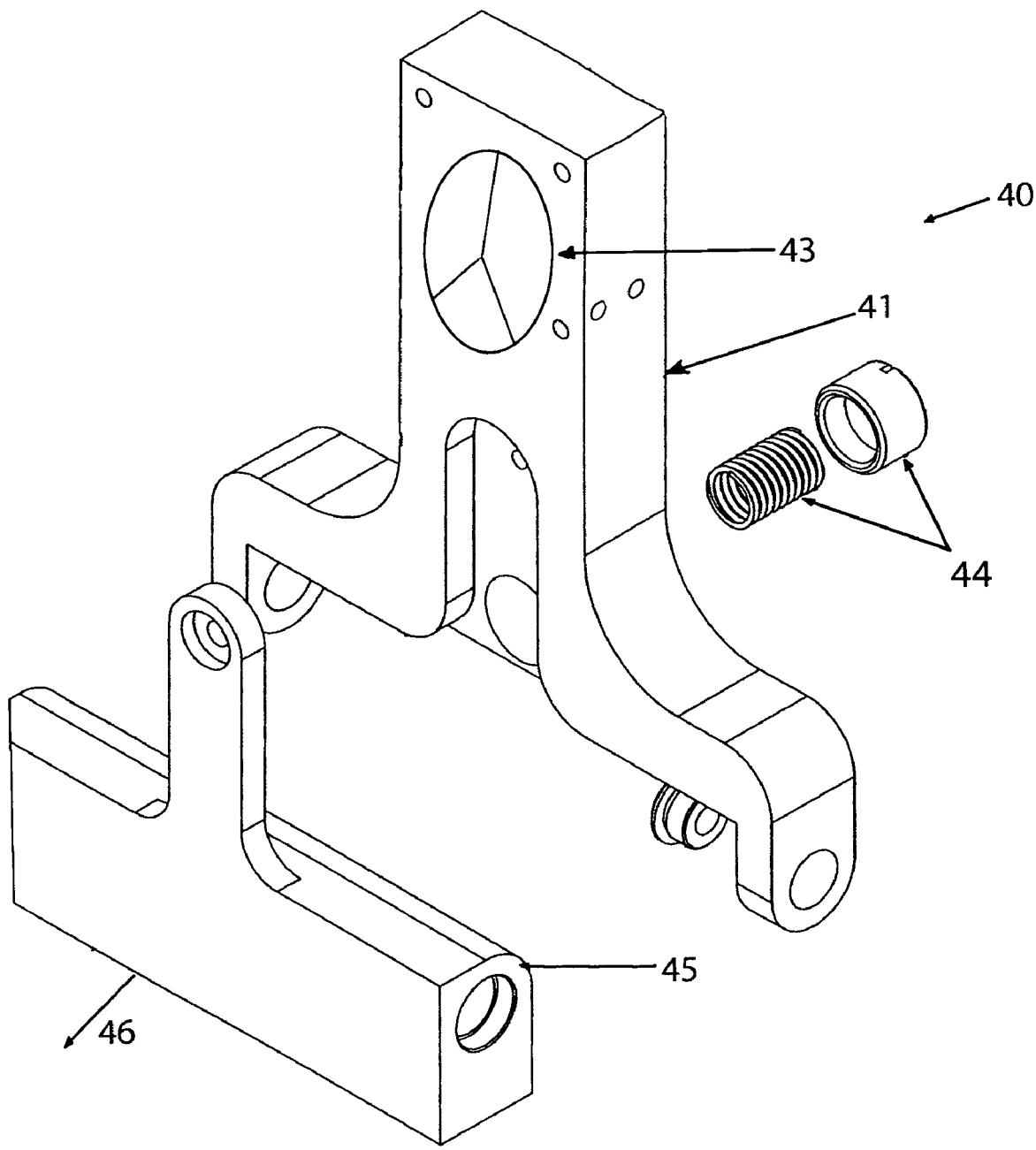
FIG. 7, depicts a collet equipped with a biased tensioner.

The present invention still further relates to a collet 40 having a collet tensioner 44. It is understood that when a filament is twisted, the length of that filament will be decreased. Accordingly, when the filament is firmly grasped at two ends the force required to twist the filament is transferred into a longitudinal tension force acting on the filament. If the force were of sufficient magnitude, the filament could break. To avoid this, at least one of the collets 40 of the cutting apparatus may be equipped with a collet tensioner 44. The collet tensioner 44 may be comprised of a simple spring as shown in FIG. 7. In the collet 40 shown in FIG. 7, the support 41 of the collet 40 is rotatable about a pin 46. The pin passes through the support 41 and the collet base 45. The collet tensioner 44 acts against the base 45 in the longitudinal direction of a filament threaded through the chuck 43 housed in the collet 40. The tension imparted on the filament by collet tensioner 44 may be adjusted by screw cap 5 which increases or decreases an initial spring tension imparted on the collet 40. This adjustment enables the apparatus to be useful for a wide variety of filament materials.

In operation, when the filament is twisted, the force of the shortening causes the collet 40 to be pulled in the longitudinal direction of the filament. The collet tensioner 44 allows for the collet 40 to move in that direction when sufficient force is imparted on the collet 40 to overcome the resisting spring force of the collet tensioner 44. The pin 46 provides an axis about which the collet 40 can rotate. This movement insures that the force imparted on the filament never exceeds the spring force of the collet tensioner 44. Accordingly, the spring force of the collet tensioner 44 can be regulated to insure that the filament is never tensioned to the point of breaking.

Figure 6:
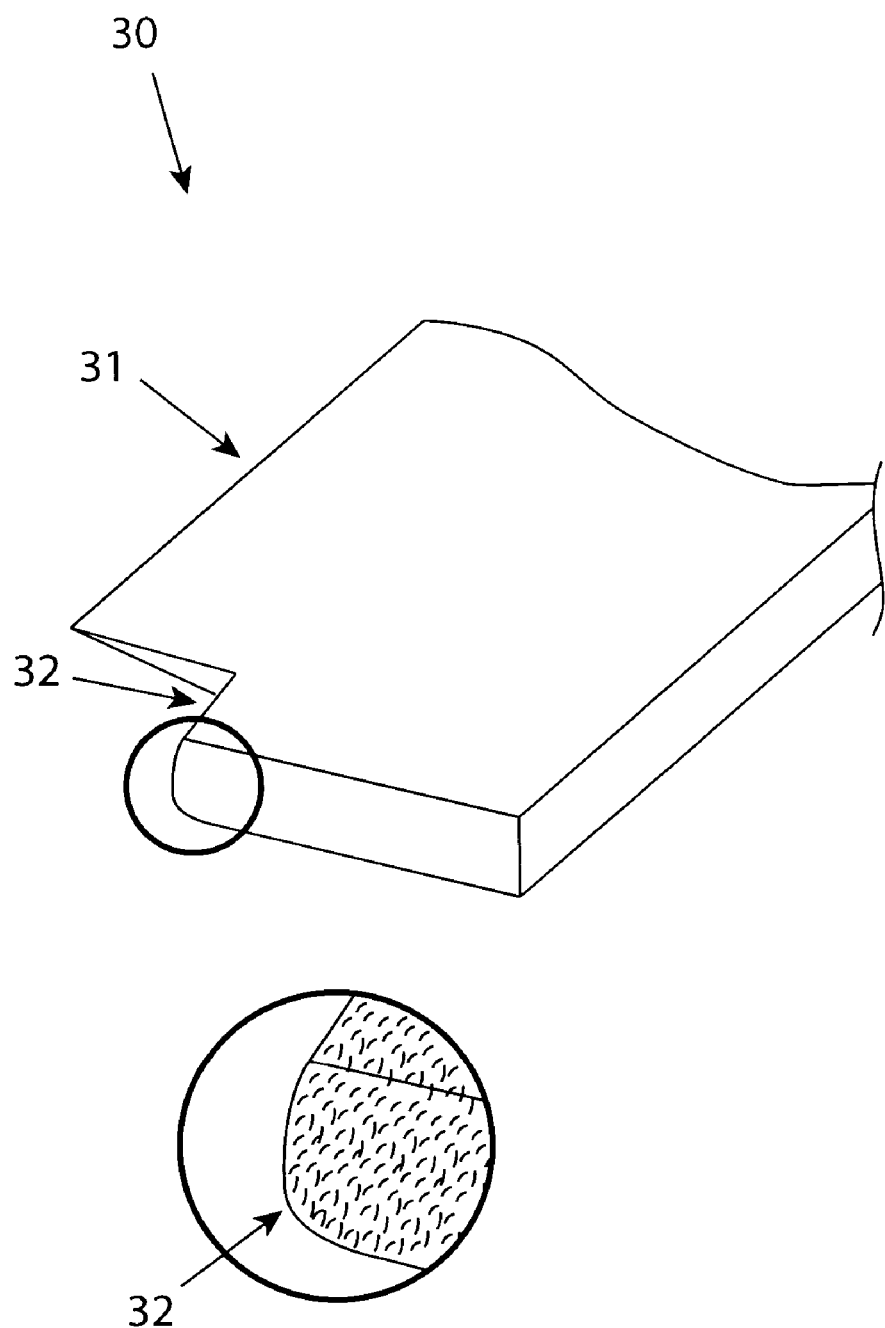
FIG. 6, depicts a perspective view of a cutting assembly with magnified view.

As shown in FIG. 6, another aspect of the present invention relates to a cutting blade 30 for cutting barbs into a filament. FIG. 6 shows a cutting blade having a sharply honed edge 31. This is the primary cutting edge of the cutting assembly and is used for the initial cutting of a barb in a filament. Following the first edge is a second edge 32. The second edge is preferably blunted, textured or rounded, as shown in the magnified view of the cutting assembly 30, FIG. 6. The textured and blunted features of cutting blade 30 act to roughen the interior surfaces of the barb section of the filament. This is preferable because it has been observed that a roughened texture on the interior surface of a barb imparts greater holding ability. This gripping ability insures that the suture is less likely to slip when threaded through tissues by a surgeon or other medical personnel. Alternatively, cutting blades with ends that are arcuate can create an arcuate shape at the base of the barb so as to reduce the sheering stress focused at the vertex of the barb.

In operation, the cutting blade is typically drawn across and into the filament to be cut. As such, the sharply honed first edge 31 cuts the barb in the filament to the desired depth and at the desired angle to the filament. The second edge 32 is subsequently drawn along the previously cut barb and roughens the interior surfaces of the barb.

In yet another aspect of the present invention the cutting blade is held by a robotic arm and performs the cutting of the filament in an articulated, motor controlled action. The robotic arm holds a plurality of cutting blades and locates the cutting blades over the filament. In one aspect of the robotic arm embodiment, the cutting blades oscillate in a cutting motion while being lowered onto the filament by the robotic arm. Further, the robotic arm may angle the cutting blades to form the barbs on the filament.

Figure 8:
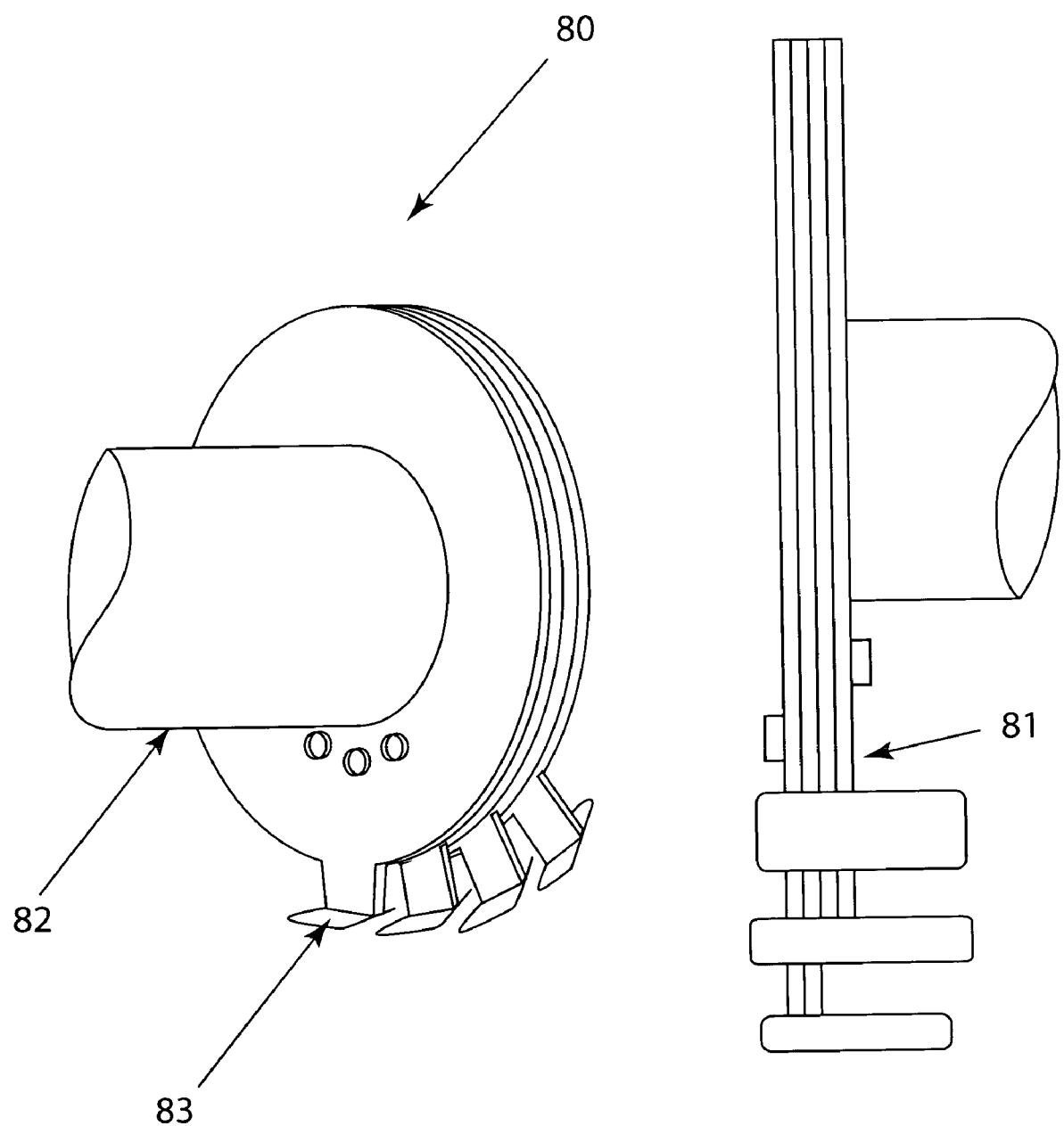
FIG. 8, depicts a rotational barb cutter mounted on a shaft.
Figure 9:
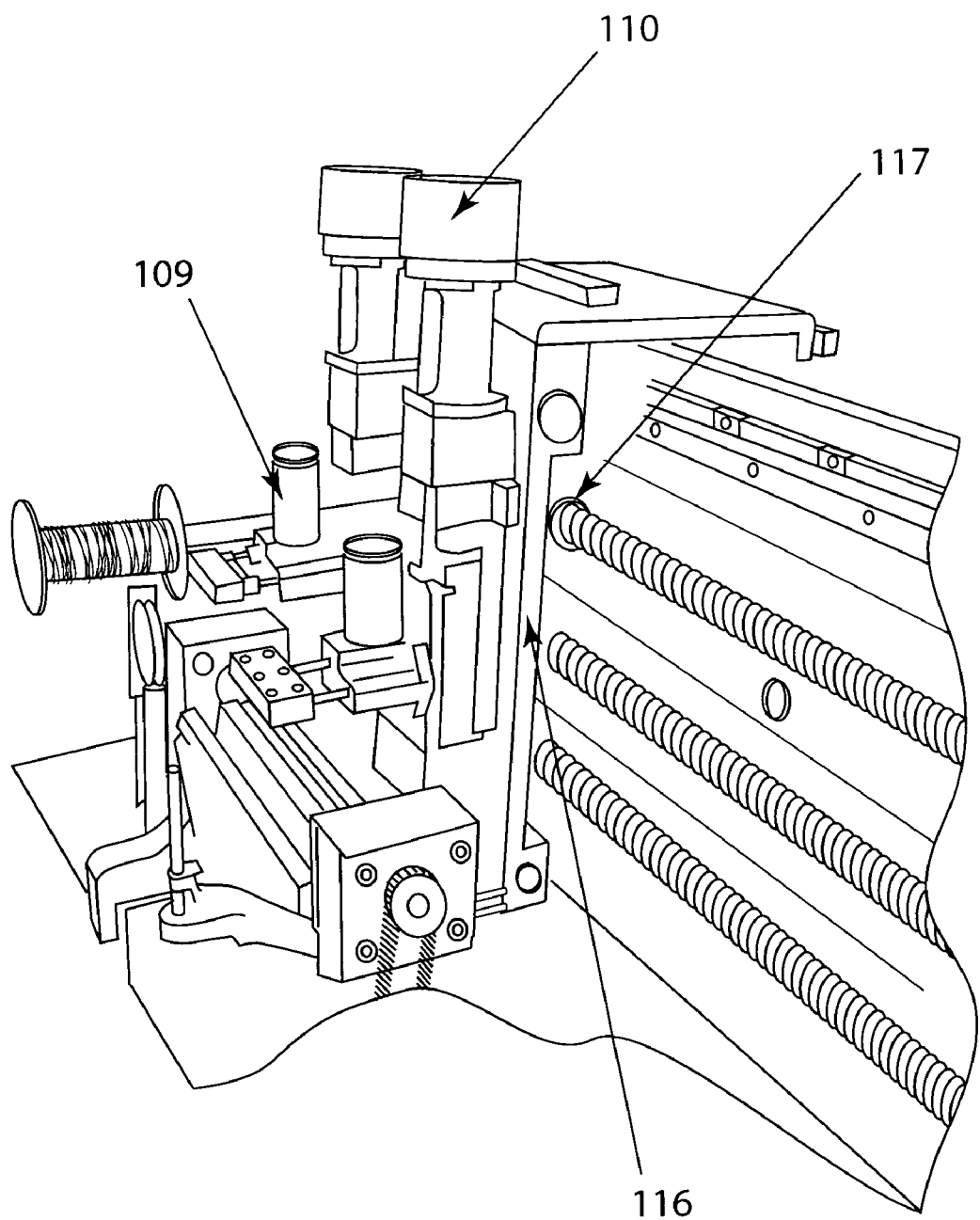
FIG. 9, a perspective view of the cutting assembly and the in-feed and out-feed collets.

Another aspect of the present invention relates to a cutter 80 that is comprised of a series of cutting disks 81 connected to a shaft 82, as shown in FIG. 8. The cutting disks have an angled tab extending from them. The tab is the cutting surface of the disk. The tab is angled at least 90 degrees from the disk. This angling allows for the barb to be displaced vertically from the filament which increases its gripping power when used. A plurality of disks are attached to a single shaft separated by spacers (not shown). On a single shaft disks with tabs facing in opposite directions can be attached to enable the cutting of barbs in both directions in a single operation. Alternatively, two cutters could be used, one for cutting the barbs in each direction. The tabs of the cutting disks are offset relative to one another such that the cutter can be positioned over a filament in which barbs are to be cut without initially contacting the filament. It is preferable that the cutter 80 makes one rotation to cut all of the barbs for a single suture, however, it may be necessary in certain applications to make more rotations particularly where a large section of suture is to be given barbs of a particular orientation. Finally, the tabs 83 may be given a variety of cutting shapes and attributes, these include but are not limited to cup shaped blades, tear dropped shaped blades, and roughed blades, as shown in FIG. 6.

While the invention has been described in connection with what is considered to be the most practical and preferred embodiment, it should be understood that this invention is not limited to the disclosed embodiments, but on the contrary, is intended to cover various modifications and equivalent arrangements included within the spirit and scope of the appended claims.

We claim:

1. An apparatus for cutting barbs into a filament for forming a barbed suture, the apparatus comprising:
   a filament supply means;
   an in-feed collet for holding the filament at a first position along the filament, the filament threaded through the in-feed collet;
   an out-feed collet for holding a filament at a second position along the filament, the second position spaced from the first position, the filament threaded through the out-feed collet;
   a holder positioned between said in-feed and out-feed collets for holding the filament between said in-feed and out-feed collets;
   a cutting assembly for cutting barbs in the filament between said in-feed and out feed collets; and
   a filament advancement means for advancing the filament.

2. The apparatus of claim 1, further comprising a tensioner for tensioning the filament held between the in-feed and out-feed collets.

3. The apparatus of claim 1, further having a cutter for cutting the filament to a desired length to form a suture after barbs have been cut into the filament.

4. The apparatus of claim 1, wherein the filament supply means is a spool having filament wrapped therein thereon.

5. The apparatus of claim 4, wherein the spool is motorized.

6. The apparatus of claim 1, further comprising a collection spool for collecting the filament after barbs have been cut in the filament.

7. The apparatus of claim 6, wherein the collection spool is motorized.

8. The apparatus of claim 1, further comprising a cut off tool for trimming the filament to a specified length to form a suture.

9. The apparatus of claim 8, wherein the suture is cut from the filament after barbs have been cut in the filament.

10. The apparatus of claim 1, wherein the filament advancement means comprises a grasping tool, and wherein the cutting assembly comprises:
    a first directional feed motor for moving a first cutter;
    a second directional feed motor for moving a second cutter; and
    a third directional feed motor for moving the grasping tool, wherein the first and second cutters cut barbs into the filament and the grasping tool advances the filament after cutting of the barbs.

11. A barb cutting apparatus for cutting barbs into a filament for forming a barbed suture, the apparatus comprising:
    a first cutter;
    a first directional feed motor for moving said first cutter;
    a second cutter;
    a second directional feed motor for moving said second cutter;
    a grasping tool for holding the filament; and
    a third directional feed motor for moving said grasping tool;
    wherein the first and second cutters cut barbs into the filament and the grasping tool advances the filament after cutting of the barbs.

12. The apparatus of claim 11 further comprising a severing blade, wherein the severing blade severs the filament after advancement to form a suture.

13. A holder for securing a suture in preparation for the cutting of barbs therein comprising:
    a bed,
    a channel arranged in the bed; and
    a plurality of orifices arranged along the channel, each orifice comprising a first end exposed in the channel and a second end connected to a suction means, wherein a suction applied to the second end creates a vacuum for securing a suture placed so as to cover at least one of the plurality of orifices.

14. A collet for holding a suture in place relative to the longitudinal axis of the suture during the cutting of barbs therein, comprising:
    a chuck support; and
    a rotatable chuck having a variably adjustable aperture housed in said support, said chuck comprising a plurality of jaws, whereby rotation of said chuck causes movement of said jaws and adjusts the aperture of said chuck to hold the suture threaded therethrough.

15. The collet as recited in claim 14, wherein said chuck comprises three jaws.

16. The collet as recited in claim 14, wherein each of said jaws has a substantially flat holding surface.

17. The collet as recited in claim 14, wherein the chuck comprises two jaws.

18. The collet as recited in claim 14, wherein each jaw has a concave holding surface.

19. The collet as recited in claim 14, wherein said chuck can be rotated about the longitudinal axis of the suture to impart twist to the suture.

20. An apparatus for cutting barbs into sutures comprising:
   at least one collet for holding a suture, wherein said at least one collet rotates in a first direction to impart twist on the suture; and
   a cutter for butting barbs on the twisted suture.

21. The apparatus as recited in claim 20, wherein said collet rotates in a second direction to untwist the suture.

22. The apparatus as recited in claim 20, further comprising:
   a first collet rotatable in a first direction for imparting twist on a suture; and
   a second collet rotatable in a second direction for removing the twist imparted to the suture.

23. An apparatus for cutting barbs into sutures comprising:
   at least one collet;
   a chuck housed in the collet; and
   at least one biased tensioner, the biased tensioner allowing the collet to move in a first direction as a suture held in the chuck is twisted, the biased tensioner moving the collet in a second direction as the suture is untwisted; wherein the movement of the collet insures that the suture receives no more than a specified tension.

24. An apparatus for cutting barbs into sutures comprising:
   a suture material supply, for feeding suture material to at least one collet, said at least one collet holding suture material along a longitudinal axis; and
   a tensioner, the tensioner further comprising at least one fixed pulley and at least one movable biased pulley, wherein the movable biased pulley imparts a force on the suture material tensioning a section of suture material held by the at least one collet.

25. An apparatus for cutting barbs into sutures, the apparatus comprising:
   a filament supply;
   a sharply honed first edge for cutting a barb into a suture to a specified depth and in a specified direction; and
   a blunt and rough second edge to impart a roughened texture to a surface of the barb.

26. A method of forming a barbed suture comprising the steps of:
   threading a filament from a filament supply through a filament tensioner and through a first and second collet;
   closing the first and second collets;
   rotating at least one of the collets in a first direction to twist the filament;
   cutting barbs in at least a first direction into the twisted filament;
   untwisting the filament and opening the collets;
   advancing the filament using a filament grasping tool;
   closing the collets; and
   severing the filament having barbs cut therein to form a suture.

27. The apparatus of claim 25, wherein the first and second edges are of unitary construction.

28. An apparatus for cutting barbs into a filament for forming a barbed suture, the apparatus comprising:
   a filament supply means;
   at least one collet for holding the filament;
   a cutting bed for resting the filament thereon;
   a cutting assembly for cutting barbs in the filament; and
   a filament advancement means for advancing the filament.

29. The apparatus of claim 28 further comprising a robotic arm assembly, said robotic arm assembly manipulating the cutting assembly to cut the barbs in the filament.

30. The apparatus of claim 25, wherein the first and second edges are fixed relative to each other.

31. A cutting blade for use in an apparatus for cutting barbs into sutures, the cutting blade comprising:
   a sharp first edge for cutting a barb into a suture; and
   a blunt edge to impart a roughened texture to a surface of the barb; the apparatus further comprising a filament supply.

32. The cutting blade of claim 31, wherein the first edge is linear.

33. The cutting blade of claim 31, wherein the second edge is rough.

34. The cutting blade of claim 31, wherein the second edge is textured.

35. The cutting blade of claim 31, wherein the second edge is rounded.

36. The cutting blade of claim 31, wherein the cutting blade has an arcuate end.

37. The cutting blade of claim 31, wherein the blade is of unitary construction.

38. The cutting blade of claim 31, wherein the first and second edges are fixed relative to each other.

39. A barb cut into a suture, the barb including a rough interior surface and made by the process comprising the steps of:
   providing a cutting blade including a sharp first edge and a blunt second edge;
   drawing the first edge across and into the suture to cut a barb; and
   drawing the second edge along the previously cut barb, roughening an interior surface of the barb.

40. A barbed suture including barbs with a rough interior surface and made by the process comprising the steps of:
   providing a cutting blade including a sharp first edge and a blunt second edge;
   drawing the first edge across and into the suture to cut a barb; and
   drawing the second edge along the previously cut barb, roughening an interior surface of the barb.

41. A method of cutting a barb into a suture, comprising:
   providing a cutting blade including a sharp first edge and a blunt second edge;
   drawing the first edge across and into the suture to cut a barb; and
   drawing the second edge along the previously cut barb, roughening a surface of the barb.

* * * * *